United States Patent
Sohn et al.

(10) Patent No.: US 12,357,686 B2
(45) Date of Patent: Jul. 15, 2025

(54) PORCINE EPIDEMIC DIARRHEA (PED) VIRUS VACCINE COMPOSITION AND PREPARATION METHOD THEREOF

(71) Applicant: BIOAPPLICATIONS INC., Gyeongsangbuk-do (KR)

(72) Inventors: Eun-Ju Sohn, Gyeongsangbuk-do (KR); Yong Jik Lee, Gyeongsangbuk-do (KR)

(73) Assignee: BIOAPPLICATIONS INC., Gyeongsangbuk-do (KR)

( * ) Notice: Subject to any disclaimer, the term of this patent is extended or adjusted under 35 U.S.C. 154(b) by 892 days.

(21) Appl. No.: 17/435,145

(22) PCT Filed: Apr. 13, 2020

(86) PCT No.: PCT/KR2020/004954
§ 371 (c)(1),
(2) Date: Aug. 31, 2021

(87) PCT Pub. No.: WO2020/213898
PCT Pub. Date: Oct. 22, 2020

(65) Prior Publication Data
US 2022/0133879 A1 May 5, 2022

(30) Foreign Application Priority Data
Apr. 16, 2019 (KR) .................. 10-2019-0044008

(51) Int. Cl.
| | | |
|---|---|---|
| *A61K 39/215* | (2006.01) | |
| *A61P 31/14* | (2006.01) | |
| *C07K 14/005* | (2006.01) | |
| *A61K 39/00* | (2006.01) | |

(52) U.S. Cl.
CPC ............ *A61K 39/215* (2013.01); *A61P 31/14* (2018.01); *C07K 14/005* (2013.01); *A61K 2039/552* (2013.01); *C12N 2770/20034* (2013.01)

(58) Field of Classification Search
None
See application file for complete search history.

(56) References Cited

U.S. PATENT DOCUMENTS

| | | | | |
|---|---|---|---|---|
| 9,339,536 B2 * | 5/2016 | Chou | .............. | A61P 31/00 |
| 2011/0014651 A1 * | 1/2011 | Chiba | .............. | C12N 9/0051 |
| | | | | 435/254.2 |
| 2013/0295065 A1 | 11/2013 | Shulman et al. | | |

FOREIGN PATENT DOCUMENTS

| | | |
|---|---|---|
| CN | 107664697 A | 2/2018 |
| KR | 1020070045817 A | 5/2007 |
| KR | 1020120066555 A | 6/2012 |
| KR | 101339703 B1 | 12/2013 |
| KR | 1020160075378 A | 6/2016 |
| KR | 1020160077239 A | 7/2016 |
| KR | 1020160132494 A | 11/2016 |
| WO | 2009158716 A1 | 12/2009 |
| WO | 2016130569 A1 | 8/2016 |
| WO | 2016130838 A1 | 8/2016 |
| WO | 2016138421 A1 | 9/2016 |
| WO | 2018135860 A1 | 7/2018 |
| WO | 2018140766 A2 | 8/2018 |
| WO | 2018140766 A3 | 8/2018 |
| WO | 2018208099 A2 | 11/2018 |
| WO | 2018213912 A1 | 11/2018 |
| WO | 2018208099 A3 | 1/2019 |

OTHER PUBLICATIONS

GenBank Accession No. AHZ45711.1 (May 2014 in IDS on Aug. 31, 2021.*
English translation of the Written opinion PCT/KR2020/004954 Apr. 2020.*
GenBank Accession No. AHZ45711.1, dated May 17, 2014; https://www.ncbi.nlm.nih.gov/protein/AHZ45711.
International Search Report (ISR) for PCT/KR2020/004954 mailed Sep. 8, 2020.
Anonymous, "Spike protein [Porcine epidemic diarrhea vims", Protein, NCBI, (May 17, 2014), Database accession No. AHZ45711, XP055751640, 2 pages.

* cited by examiner

*Primary Examiner* — Agnieszka Boesen
(74) *Attorney, Agent, or Firm* — Riverside Law LLP (57) ABSTRACT

The present invention relates to: a porcine epidemic diarrhea (PED) virus protein comprising an amino acid sequence represented by SEQ ID NO:5; a vaccine composition comprising same; and the like.

8 Claims, 3 Drawing Sheets

Specification includes a Sequence Listing.

FIG.1

| BiP | PEDV-S1 | pFc2 | HDEL |

| Serum | | Pre | Post | Pre | Post |
|---|---|---|---|---|---|
| NC<br>negative control | 1 | 0.08 | 0.09 | | |
| | 2 | 0.10 | 0.10 | | |
| | 3 | 0.08 | 0.11 | | |
| | 4 | 0.10 | 0.11 | | |
| | 5 | 0.11 | 0.09 | | |
| PC<br>positive control | 6 | 0.07 | 1.31 | | |
| | 7 | 0.09 | 0.49 | | |
| | 8 | 0.07 | 2.04 | | |
| | 9 | 0.08 | 0.79 | | |
| | 10 | 0.09 | 2.20 | | |
| PEDV-S1:pFC2<br>administration | 11 | 0.09 | 3.05 | | |
| | 12 | 0.08 | 2.06 | | |
| | 13 | 0.06 | 3.03 | | |
| | 14 | 0.06 | 2.88 | | |
| | 15 | 0.07 | 2.19 | | |

```
                        SEQUENCE LISTING

<160> NUMBER OF SEQ ID NOS: 13

<210> SEQ ID NO 1
<211> LENGTH: 2148
<212> TYPE: DNA
<213> ORGANISM: Artificial Sequence
<220> FEATURE:
<223> OTHER INFORMATION: PEDV-S1

<400> SEQUENCE: 1
caagatgtca ctagatgttc tgcaaacacg aatttccggc gtttcttttc aaaattcaac      60
gttcaagcac ccgcagtggt tgtcctcgga ggttatctgc ctataggcga gaatcagggt     120
gtgaacagta cttggtattg tgctggtcaa caccctacag ctagcggcgt tcacggcatc     180
tttgtatcac atattagagg aggacatggt tttgaaattg ggatctcaca ggaaccttt      240 gatcctagtg gttatcaact ttacttacac aaagcgacta atggtaatac aaatgctacc     300
gccaggctta gaatttgtca gtttccaagc atcaagacct tgggcccgac tgcaaacaac     360
```

-continued

```
gatgttacga ccggtaggaa ttgtcttttc aataaggcaa ttccagctca tatgtctgaa      420
cattctgttg taggtataac atgggataac gatagagtta ctgtgttttc cgataaaatt      480
tactatttct acttcaagaa cgactggtcg cgagtcgcta ctaagtgcta taatagtggt      540
ggatgcgcta tgcagtacgt gtacgagcca acatactata tgttgaatgt tacctctgct      600
ggggaggacg ggatttccta tcaaccttgc acagccaatt gcatcggata tgctgctaat      660 gttttgcta ctgagcctaa cggtcacatc ccagaaggat tttcttcaa taactggttc       720 cttcttagca atgactctac tctagtacat ggaaaagtag tgtcgaatca accgctgctc      780
gtgaattgtc ttcttgctat accaaagatc tacggacttg acaatttttt ctcctttaac      840
caaactatcg acggggtctg taatggcgct gctgttcaaa gagcccccga ggctcttcga      900
tttaatatta atgataccag cgttattctt gctgaaggct cgatcgttct tcatactgct      960
ctggggacta acttttcttt tgtgtgcagt aactcttcta atccacacct tgccactttt     1020
gctatgccac ttggggccac acaggttcca tactactgtt ttctgaaggt ggacacttat     1080
aattctactg tctacaagtt tctcgctgtt ttgccaccaa ctgtcagaga atagttatt     1140 actaagtacg gtgatgtata tgttaacggg tttgaatatc tacatctagg ccttctcgat    1200
gctgttacta tcaatttcac tggccatgga acagacgatg atgttagtgg cttctggacg    1260
atagcctcta caaatttcgt tgatgctctt atagaagtcc aaggaactgc tattcagcgt    1320
atcctttact gcgacgatcc agtctcacag cttaaatgtt ctcaggttgc attcgatctc    1380
gatgatggat tttatcctat ttcttcgaga aacctcctgt ctcacgagca accaatatct    1440
ttcgtgactc ttccctcttt taacgatcat tcttttgtta atataaccgt ttcagcttcc    1500
tttggaggac attctggagc taaccttatt gcttctgaca ctacgattaa tgggttctcc    1560
tccttctgcg tcgacacaag acaattcacc atttctcttt tctacaatgt tactaattct    1620
tatggatacg tttccaagtc tcaagactct aattgcccgt ttactcttca gtctgttaac    1680
gattatcttt cttttttctaa gttttgtgtt tctacctctc ttcttgcgtc tgcttgcacg    1740
attgatcttt tcggataccc agagtttggc tctggagtta aattcactag ccttatttc    1800 cagtttacta agggagagct aattactgga actccaaaac ctcttgaagg agtgactgat    1860
gtttctttta tgacgcttga tgtgtgtact aagtatacta tctacggggtt caagggagag    1920 ggtattataa ctcttactaa ctcttctttt cttgctggtg tttattacac tagcgactct    1980
ggacaattac ttgctttcaa aaacgttact tctggagcgg tttattctgt gactccatgt    2040
tcgttctccg aacaggccgc ttatgttgat gacgatattg ttggtgtcat ttcaagcctt    2100
tcctcatcta cctttaacag caccagggaa cttccaggat ttttctat                2148
```

<210> SEQ ID NO 2
<211> LENGTH: 273
<212> TYPE: DNA
<213> ORGANISM: Artificial Sequence
<220> FEATURE:
<223> OTHER INFORMATION: chapherone binding protein(BiP)

<400> SEQUENCE: 2

```
atggctcgct cgtttggagc taacagtacc gttgtgttgg cgatcatctt cttcggtgag       60
tgattttccg atcttcttct ccgatttaga tctcctctac attgttgctt aatctcagaa      120
ccttttttcg ttgttcctgg atctgaatgt gtttgtttgc aatttcacga tcttaaaagg      180
ttagatctcg attggtattg acgattggaa tctttacgat tcaggatgtt ttatttgcgt      240
tgtcctctgc aatagaagag gctacgaagt taa                                   273
```

<210> SEQ ID NO 3
<211> LENGTH: 681
<212> TYPE: DNA
<213> ORGANISM: Artificial Sequence
<220> FEATURE:
<223> OTHER INFORMATION: porcine Fc2

<400> SEQUENCE: 3

```
gttggaagac catgccctat atgtcctgct tgtgaaggtc caggtccctc tgctttata      60
ttcccaccaa agccgaagga taccttgatg atttcacgta caccacaagt tacttgtgtt   120
gttgtggatg tttcacaaga aaatcctgag gtacaattca gctggtatgt tgatggggta   180
gaagtgcaca ctgcacagac tcgaccaaag gaggcccagt taactcgac ttatagagtt    240
gtttctgttc tcccaatcca acacgaagat tggctgaagg gcaaggaatt tgaatgcaag   300
gttaacaata agatctacc agcaccaatt accaggatta tttctaaggc aaaaggaccc    360
tccagagagc cccaagttta cacattgtct ccttctgctg aggagcttag tagaagtaaa   420
gtgagcatta cctgcttagt gacgggattc taccctccag acatcgacgt cgaatggaaa   480
tctaatggtc aacctgagcc agaaggtaac tataggacta ctccaccaca acaggacgtc   540
gatggcacat actttcttta ttcaaaactt gctgtcgata aggcaagttg gcaaagagga   600
gatccatttc agtgtgctgt aatgcatgag gctttgcata atcattatac acagaaatca   660
gtttctaaaa cacaagggaa a                                              681
```

<210> SEQ ID NO 4
<211> LENGTH: 12
<212> TYPE: DNA
<213> ORGANISM: Artificial Sequence
<220> FEATURE:
<223> OTHER INFORMATION: HDEL

<400> SEQUENCE: 4

```
catgatgagc tc                                                         12
```

<210> SEQ ID NO 5
<211> LENGTH: 716
<212> TYPE: PRT
<213> ORGANISM: Artificial Sequence
<220> FEATURE:
<223> OTHER INFORMATION: PEDV-S1 AA

<400> SEQUENCE: 5

```
Gln Asp Val Thr Arg Cys Ser Ala Asn Thr Asn Phe Arg Arg Phe Phe
1               5                   10                  15

Ser Lys Phe Asn Val Gln Ala Pro Ala Val Val Val Leu Gly Gly Tyr
            20                  25                  30

Leu Pro Ile Gly Glu Asn Gln Gly Val Asn Ser Thr Trp Tyr Cys Ala
        35                  40                  45

Gly Gln His Pro Thr Ala Ser Gly Val His Gly Ile Phe Val Ser His
    50                  55                  60

Ile Arg Gly Gly His Gly Phe Glu Ile Gly Ile Ser Gln Glu Pro Phe
65                  70                  75                  80

Asp Pro Ser Gly Tyr Gln Leu Tyr Leu His Lys Ala Thr Asn Gly Asn
                85                  90                  95

Thr Asn Ala Thr Ala Arg Leu Arg Ile Cys Gln Phe Pro Ser Ile Lys
            100                 105                 110

Thr Leu Gly Pro Thr Ala Asn Asn Asp Val Thr Thr Gly Arg Asn Cys
```

```
            115                 120                 125
Leu Phe Asn Lys Ala Ile Pro Ala His Met Ser Glu His Ser Val Val
130                 135                 140

Gly Ile Thr Trp Asp Asn Asp Arg Val Thr Val Phe Ser Asp Lys Ile
145                 150                 155                 160

Tyr Tyr Phe Tyr Phe Lys Asn Asp Trp Ser Arg Val Ala Thr Lys Cys
                165                 170                 175

Tyr Asn Ser Gly Gly Cys Ala Met Gln Tyr Val Tyr Glu Pro Thr Tyr
            180                 185                 190

Tyr Met Leu Asn Val Thr Ser Ala Gly Glu Asp Gly Ile Ser Tyr Gln
        195                 200                 205

Pro Cys Thr Ala Asn Cys Ile Gly Tyr Ala Ala Asn Val Phe Ala Thr
    210                 215                 220

Glu Pro Asn Gly His Ile Pro Glu Gly Phe Ser Phe Asn Asn Trp Phe
225                 230                 235                 240

Leu Leu Ser Asn Asp Ser Thr Leu Val His Gly Lys Val Val Ser Asn
                245                 250                 255

Gln Pro Leu Leu Val Asn Cys Leu Leu Ala Ile Pro Lys Ile Tyr Gly
            260                 265                 270

Leu Gly Gln Phe Phe Ser Phe Asn Gln Thr Ile Asp Gly Val Cys Asn
        275                 280                 285

Gly Ala Ala Val Gln Arg Ala Pro Glu Ala Leu Arg Phe Asn Ile Asn
    290                 295                 300

Asp Thr Ser Val Ile Leu Ala Glu Gly Ser Ile Val Leu His Thr Ala
305                 310                 315                 320

Leu Gly Thr Asn Phe Ser Phe Val Cys Ser Asn Ser Ser Asn Pro His
                325                 330                 335

Leu Ala Thr Phe Ala Met Pro Leu Gly Ala Thr Gln Val Pro Tyr Tyr
            340                 345                 350

Cys Phe Leu Lys Val Asp Thr Tyr Asn Ser Thr Val Tyr Lys Phe Leu
        355                 360                 365

Ala Val Leu Pro Pro Thr Val Arg Glu Ile Val Ile Thr Lys Tyr Gly
    370                 375                 380

Asp Val Tyr Val Asn Gly Phe Glu Tyr Leu His Leu Gly Leu Leu Asp
385                 390                 395                 400

Ala Val Thr Ile Asn Phe Thr Gly His Gly Thr Asp Asp Asp Val Ser
                405                 410                 415

Gly Phe Trp Thr Ile Ala Ser Thr Asn Phe Val Asp Ala Leu Ile Glu
            420                 425                 430

Val Gln Gly Thr Ala Ile Gln Arg Ile Leu Tyr Cys Asp Asp Pro Val
        435                 440                 445

Ser Gln Leu Lys Cys Ser Gln Val Ala Phe Asp Leu Asp Asp Gly Phe
    450                 455                 460

Tyr Pro Ile Ser Ser Arg Asn Leu Leu Ser His Glu Gln Pro Ile Ser
465                 470                 475                 480

Phe Val Thr Leu Pro Ser Phe Asn Asp His Ser Phe Val Asn Ile Thr
                485                 490                 495

Val Ser Ala Ser Phe Gly Gly His Ser Gly Ala Asn Leu Ile Ala Ser
            500                 505                 510

Asp Thr Thr Ile Asn Gly Phe Ser Ser Phe Cys Val Asp Thr Arg Gln
        515                 520                 525

Phe Thr Ile Ser Leu Phe Tyr Asn Val Thr Asn Ser Tyr Gly Tyr Val
    530                 535                 540
```

```
Ser Lys Ser Gln Asp Ser Asn Cys Pro Phe Thr Leu Gln Ser Val Asn
545                 550                 555                 560

Asp Tyr Leu Ser Phe Ser Lys Phe Cys Val Ser Thr Ser Leu Leu Ala
                565                 570                 575

Ser Ala Cys Thr Ile Asp Leu Phe Gly Tyr Pro Glu Phe Gly Ser Gly
            580                 585                 590

Val Lys Phe Thr Ser Leu Tyr Phe Gln Phe Thr Lys Gly Glu Leu Ile
            595                 600                 605

Thr Gly Thr Pro Lys Pro Leu Glu Gly Val Thr Asp Val Ser Phe Met
        610                 615                 620

Thr Leu Asp Val Cys Thr Lys Tyr Thr Ile Tyr Gly Phe Lys Gly Glu
625                 630                 635                 640

Gly Ile Ile Thr Leu Thr Asn Ser Ser Phe Leu Ala Gly Val Tyr Tyr
                645                 650                 655

Thr Ser Asp Ser Gly Gln Leu Leu Ala Phe Lys Asn Val Thr Ser Gly
            660                 665                 670

Ala Val Tyr Ser Val Thr Pro Cys Ser Phe Ser Glu Gln Ala Ala Tyr
            675                 680                 685

Val Asp Asp Ile Val Gly Val Ile Ser Ser Leu Ser Ser Ser Ser Thr
        690                 695                 700

Phe Asn Ser Thr Arg Glu Leu Pro Gly Phe Phe Tyr
705                 710                 715

<210> SEQ ID NO 6
<211> LENGTH: 4
<212> TYPE: PRT
<213> ORGANISM: Artificial Sequence
<220> FEATURE:
<223> OTHER INFORMATION: KDEL

<400> SEQUENCE: 6

Lys Asp Glu Leu
1

<210> SEQ ID NO 7
<211> LENGTH: 4
<212> TYPE: PRT
<213> ORGANISM: Artificial Sequence
<220> FEATURE:
<223> OTHER INFORMATION: HDEL AA

<400> SEQUENCE: 7

His Asp Glu Leu
1

<210> SEQ ID NO 8
<211> LENGTH: 6
<212> TYPE: PRT
<213> ORGANISM: Artificial Sequence
<220> FEATURE:
<223> OTHER INFORMATION: SEKDEL

<400> SEQUENCE: 8

Ser Glu Lys Asp Glu Leu
1               5

<210> SEQ ID NO 9
<211> LENGTH: 5
<212> TYPE: PRT
<213> ORGANISM: Artificial Sequence
<220> FEATURE:
```

```
<223> OTHER INFORMATION: KHEDL

<400> SEQUENCE: 9

Lys His Glu Asp Leu
1               5

<210> SEQ ID NO 10
<211> LENGTH: 4
<212> TYPE: PRT
<213> ORGANISM: Artificial Sequence
<220> FEATURE:
<223> OTHER INFORMATION: KEEL

<400> SEQUENCE: 10

Lys Glu Glu Leu
1

<210> SEQ ID NO 11
<211> LENGTH: 6
<212> TYPE: PRT
<213> ORGANISM: Artificial Sequence
<220> FEATURE:
<223> OTHER INFORMATION: SEHEDL

<400> SEQUENCE: 11

Ser Glu His Glu Asp Leu
1               5

<210> SEQ ID NO 12
<211> LENGTH: 3131
<212> TYPE: DNA
<213> ORGANISM: Artificial Sequence
<220> FEATURE:
<223> OTHER INFORMATION: Full vector

<400> SEQUENCE: 12
atggctcgct cgtttggagc taacagtacc gttgtgttgg cgatcatctt cttcggtgag      60
tgattttccg atcttcttct ccgatttaga tctcctctac attgttgctt aatctcagaa     120
ccttttttcg ttgttcctgg atctgaatgt gtttgtttgc aatttcacga tcttaaaagg     180
ttagatctcg attggtattg acgattggaa tctttacgat ttcaggatgt ttatttgcgt     240
tgtcctctgc aatagaagag gctacgaagt taaggatcct gcaagatgtc actagatgtt     300
ctgcaaacac gaatttccgg cgtttctttt caaaattcaa cgttcaagca cccgcagtgg     360
ttgtcctcgg aggttatctg cctataggcg agaatcaggg tgtgaacagt acttggtatt     420
gtgctggtca acaccctaca gctagcggcg ttcacggcat ctttgtatca catattagag     480
gaggacatgg ttttgaaatt gggatctcac aggaaccttt tgatcctagt ggttatcaac     540
tttacttaca caaagcgact aatggtaata caaatgctac cgccaggctt agaatttgtc     600
agtttccaag catcaagacc ttgggcccga ctgcaaacaa cgatgttacg accggtagga     660
attgtctttt caataaggca attccagctc atatgtctga acattctgtt gtaggtataa     720
catgggataa cgatagagtt actgtgtttt ccgataaaat ttactatttc tacttcaaga     780
acgactggtc gcgagtcgct actaagtgct ataatagtgg tggatgcgct atgcagtacg     840
tgtacgagcc aacatactat atgttgaatg ttacctctgc tggggaggac gggatttcct     900
atcaaccttg cacagccaat tgcatcggat atgctgctaa tgttttttgct actgagccta     960 acggtcacat cccagaagga ttttctttca taactggtt ccttcttagc aatgactcta    1020
ctctagtaca tggaaaagta gtgtcgaatc aaccgctgct cgtgaattgt cttcttgcta    1080
```

```
taccaaagat ctacggactt ggacaatttt tctcctttaa ccaaactatc gacggggtct    1140
gtaatggcgc tgctgttcaa agagcccccg aggctcttcg atttaatatt aatgatacca    1200
gcgttattct tgctgaaggc tcgatcgttc ttcatactgc tctggggact aacttttctt    1260
ttgtgtgcag taactcttct aatccacacc ttgccacttt tgctatgcca cttggggcca    1320
cacaggttcc atactactgt tttctgaagg tggacactta taattctact gtctacaagt    1380
ttctcgctgt tttgccacca actgtcagag aaatagttat tactaagtac ggtgatgtat    1440
atgttaacgg gtttgaatat ctacatctag gccttctcga tgctgttact atcaatttca    1500
ctggccatgg aacagacgat gatgttagtg gcttctggac gatagcctct acaaatttcg    1560
ttgatgctct tatagaagtc caaggaactg ctattcaacg tatcctttac tgcgacgatc    1620
cagtctcaca gcttaaatgt tctcaggttg cattcgatct cgatgatgga ttttatccta    1680
tttcttcgag aaacctcctg tctcacgagc aaccaatatc tttcgtgact cttccctctt    1740
ttaacgatca ttcttttgtt aatataaccg tttcagcttc ctttggagga cattctggag    1800
ctaaccttat tgcttctgac actacgatta atgggttctc ctccttctgc gtcgacacaa    1860
gacaattcac catttctctt ttctacaatg ttactaattc ttatggatac gtttccaagt    1920
ctcaagactc taattgcccg tttactcttc agtctgttaa cgattatctt tcttttttcta   1980
agttttgtgt ttctacctct cttcttgcgt ctgcttgcac gattgatctt ttcggatacc    2040
cagagtttgg ctctggagtt aaattcacta gcctttattt ccagtttact aagggagagc    2100
taattactgg aactccaaaa cctcttgaag gagtgactga tgtttctttt atgacgcttg    2160
atgtgtgtac taagtatact atctacgggt tcaaggagag gggtattata actcttacta    2220
actcttcttt tcttgctggt gtttattaca ctagcgactc tggacaatta cttgctttca    2280
aaaacgttac ttctggagcg gtttattctg tgactccatg ttcgttctcc gaacaggccg    2340
cttatgttga tgacgatatt gttggtgtca tttcaagcct ttcctcatct accttttaaca   2400
gcaccaggga acttccagga ttttctatc cccgggcagt tggaagacca tgccctatat    2460
gtcctgcttg tgaaggtcca ggtccctctg cttttatatt cccaccaaag ccgaaggata    2520
ccttgatgat ttcacgtaca ccacaagtta cttgtgttgt tgtggatgtt tcacaagaaa    2580
atcctgaggt acaattcagc tggtatgttg atgggggtaga agtgcacact gcacagactc   2640
gaccaaagga ggcccagttt aactcgactt atagagttgt ttctgttctc ccaatccaac    2700
acgaagattg gctgaagggc aaggaatttg aatgcaaggt taacaataaa gatctaccag    2760
caccaattac caggattatt tctaaggcaa aaggaccctc cagagagccc caagtttaca    2820
cattgtctcc ttctgctgag gagcttagta gaagtaaagt gagcattacc tgcttagtga    2880
cgggattcta ccctccagac atcgacgtcg aatggaaatc taatggtcaa cctgagccag    2940
aaggtaacta taggactact ccaccacaac aggacgtcga tggcacatac tttctttatt    3000
caaaacttgc tgtcgataag gcaagttggc aaagaggaga tccatttcag tgtgctgtaa    3060
tgcatgaggc tttgcataat cattatacac agaaatcagt ttctaaaaca caagggaaac    3120
atgatgagct c                                                        3131
```

<210> SEQ ID NO 13
<211> LENGTH: 960
<212> TYPE: PRT
<213> ORGANISM: Artificial Sequence
<220> FEATURE:
<223> OTHER INFORMATION: Full vector AA

<400> SEQUENCE: 13

```
Ile Glu Glu Ala Thr Lys Leu Arg Ile Leu Gln Asp Val Thr Arg Cys
1               5                   10                  15

Ser Ala Asn Thr Asn Phe Arg Arg Phe Phe Ser Lys Phe Asn Val Gln
            20                  25                  30

Ala Pro Ala Val Val Leu Gly Gly Tyr Leu Pro Ile Gly Glu Asn
        35                  40                  45

Gln Gly Val Asn Ser Thr Trp Tyr Cys Ala Gly Gln His Pro Thr Ala
    50                  55                  60

Ser Gly Val His Gly Ile Phe Val Ser His Ile Arg Gly Gly His Gly
65                  70                  75                  80

Phe Glu Ile Gly Ile Ser Gln Glu Pro Phe Asp Pro Ser Gly Tyr Gln
                85                  90                  95

Leu Tyr Leu His Lys Ala Thr Asn Gly Asn Thr Asn Ala Thr Ala Arg
            100                 105                 110

Leu Arg Ile Cys Gln Phe Pro Ser Ile Lys Thr Leu Gly Pro Thr Ala
            115                 120                 125

Asn Asn Asp Val Thr Thr Gly Arg Asn Cys Leu Phe Asn Lys Ala Ile
    130                 135                 140

Pro Ala His Met Ser Glu His Ser Val Val Gly Ile Thr Trp Asp Asn
145                 150                 155                 160

Asp Arg Val Thr Val Phe Ser Asp Lys Ile Tyr Tyr Phe Tyr Phe Lys
                165                 170                 175

Asn Asp Trp Ser Arg Val Ala Thr Lys Cys Tyr Asn Ser Gly Gly Cys
            180                 185                 190

Ala Met Gln Tyr Val Tyr Glu Pro Thr Tyr Tyr Met Leu Asn Val Thr
        195                 200                 205

Ser Ala Gly Glu Asp Gly Ile Ser Tyr Gln Pro Cys Thr Ala Asn Cys
210                 215                 220

Ile Gly Tyr Ala Ala Asn Val Phe Ala Thr Glu Pro Asn Gly His Ile
225                 230                 235                 240

Pro Glu Gly Phe Ser Phe Asn Asn Trp Phe Leu Leu Ser Asn Asp Ser
                245                 250                 255

Thr Leu Val His Gly Lys Val Val Ser Asn Gln Pro Leu Leu Val Asn
            260                 265                 270

Cys Leu Leu Ala Ile Pro Lys Ile Tyr Gly Leu Gly Gln Phe Phe Ser
    275                 280                 285

Phe Asn Gln Thr Ile Asp Gly Val Cys Asn Gly Ala Ala Val Gln Arg
    290                 295                 300

Ala Pro Glu Ala Leu Arg Phe Asn Ile Asn Asp Thr Ser Val Ile Leu
305                 310                 315                 320

Ala Glu Gly Ser Ile Val Leu His Thr Ala Leu Gly Thr Asn Phe Ser
                325                 330                 335

Phe Val Cys Ser Asn Ser Ser Asn Pro His Leu Ala Thr Phe Ala Met
            340                 345                 350

Pro Leu Gly Ala Thr Gln Val Pro Tyr Tyr Cys Phe Leu Lys Val Asp
            355                 360                 365

Thr Tyr Asn Ser Thr Val Tyr Lys Phe Leu Ala Val Leu Pro Pro Thr
    370                 375                 380

Val Arg Glu Ile Val Ile Thr Lys Tyr Gly Asp Val Tyr Val Asn Gly
385                 390                 395                 400

Phe Glu Tyr Leu His Leu Gly Leu Leu Asp Ala Val Thr Ile Asn Phe
                405                 410                 415
```

```
Thr Gly His Gly Thr Asp Asp Val Ser Gly Phe Trp Thr Ile Ala
            420             425             430
Ser Thr Asn Phe Val Asp Ala Leu Ile Glu Val Gln Gly Thr Ala Ile
        435             440             445
Gln Arg Ile Leu Tyr Cys Asp Pro Val Ser Gln Leu Lys Cys Ser
    450             455             460
Gln Val Ala Phe Asp Leu Asp Asp Gly Phe Tyr Pro Ile Ser Ser Arg
465             470             475             480
Asn Leu Leu Ser His Glu Gln Pro Ile Ser Phe Val Thr Leu Pro Ser
            485             490             495
Phe Asn Asp His Ser Phe Val Asn Ile Thr Val Ser Ala Ser Phe Gly
            500             505             510
Gly His Ser Gly Ala Asn Leu Ile Ala Ser Asp Thr Thr Ile Asn Gly
        515             520             525
Phe Ser Ser Phe Cys Val Asp Thr Arg Gln Phe Thr Ile Ser Leu Phe
        530             535             540
Tyr Asn Val Thr Asn Ser Tyr Gly Tyr Val Ser Lys Ser Gln Asp Ser
545             550             555             560
Asn Cys Pro Phe Thr Leu Gln Ser Val Asn Asp Tyr Leu Ser Phe Ser
            565             570             575
Lys Phe Cys Val Ser Thr Ser Leu Leu Ala Ser Ala Cys Thr Ile Asp
            580             585             590
Leu Phe Gly Tyr Pro Glu Phe Gly Ser Gly Val Lys Phe Thr Ser Leu
        595             600             605
Tyr Phe Gln Phe Thr Lys Gly Glu Leu Ile Thr Gly Thr Pro Lys Pro
    610             615             620
Leu Glu Gly Val Thr Asp Val Ser Phe Met Thr Leu Asp Val Cys Thr
625             630             635             640
Lys Tyr Thr Ile Tyr Gly Phe Lys Gly Glu Gly Ile Ile Thr Leu Thr
            645             650             655
Asn Ser Ser Phe Leu Ala Gly Val Tyr Tyr Thr Ser Asp Ser Gly Gln
            660             665             670
Leu Leu Ala Phe Lys Asn Val Thr Ser Gly Ala Val Tyr Ser Val Thr
        675             680             685
Pro Cys Ser Phe Ser Glu Gln Ala Ala Tyr Val Asp Asp Asp Ile Val
        690             695             700
Gly Val Ile Ser Ser Leu Ser Ser Ser Thr Phe Asn Ser Thr Arg Glu
705             710             715             720
Leu Pro Gly Phe Phe Tyr Pro Arg Ala Val Gly Arg Pro Cys Pro Ile
            725             730             735
Cys Pro Ala Cys Glu Gly Pro Gly Pro Ser Ala Phe Ile Phe Pro Pro
            740             745             750
Lys Pro Lys Asp Thr Leu Met Ile Ser Arg Thr Pro Gln Val Thr Cys
        755             760             765
Val Val Val Asp Val Ser Gln Glu Asn Pro Glu Val Gln Phe Ser Trp
        770             775             780
Tyr Val Asp Gly Val Glu Val His Thr Ala Gln Thr Arg Pro Lys Glu
785             790             795             800
Ala Gln Phe Asn Ser Thr Tyr Arg Val Val Ser Val Leu Pro Ile Gln
            805             810             815
His Glu Asp Trp Leu Lys Gly Lys Glu Phe Glu Cys Lys Val Asn Asn
            820             825             830
Lys Asp Leu Pro Ala Pro Ile Thr Arg Ile Ile Ser Lys Ala Lys Gly
```

-continued

```
              835                 840                 845
Pro Ser Arg Glu Pro Gln Val Tyr Thr Leu Ser Pro Ser Ala Glu Glu
        850                 855                 860

Leu Ser Arg Ser Lys Val Ser Ile Thr Cys Leu Val Thr Gly Phe Tyr
865                 870                 875                 880

Pro Pro Asp Ile Asp Val Glu Trp Lys Ser Asn Gly Gln Pro Glu Pro
                885                 890                 895

Glu Gly Asn Tyr Arg Thr Thr Pro Pro Gln Gln Asp Val Asp Gly Thr
                900                 905                 910

Tyr Phe Leu Tyr Ser Lys Leu Ala Val Asp Lys Ala Ser Trp Gln Arg
            915                 920                 925

Gly Asp Pro Phe Gln Cys Ala Val Met His Glu Ala Leu His Asn His
        930                 935                 940

Tyr Thr Gln Lys Ser Val Ser Lys Thr Gln Gly Lys His Asp Glu Leu
945                 950                 955                 960
```

PORCINE EPIDEMIC DIARRHEA (PED) VIRUS VACCINE COMPOSITION AND PREPARATION METHOD THEREOF

CROSS-REFERENCE TO RELATED APPLICATIONS

This application is a U.S. National Phase Application filed under 35 U.S.C. § 371 claiming benefit to International Patent Application No. PCT/KR2020/004954, filed on Apr. 13, 2020, which claims the benefit of priority from Korean Patent Application No. 10-2019-0044008 filed on Apr. 16, 2019, the contents of each of which are incorporated herein by reference in their entirety

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0121-00US_Sequence_Listing_ST25.txt" in ASCII format. The text file containing the Sequence Listing of the present application was created on Aug. 31, 2021 and is 24,611 bytes in size.

TECHNICAL FIELD

The present invention relates to a porcine epidemic diarrhea virus vaccine composition which includes a porcine epidemic diarrhea virus S1 protein having an amino acid sequence represented by SEQ ID NO: 5 as an active ingredient, and the like

BACKGROUND ART

Porcine epidemic diarrhea (PED) is a fatal and highly contagious porcine intestinal disease, which is characterized by acute diarrhea, vomiting and dehydration, and causes high mortality in newborn piglets. This disease was first reported in England in 1971, and had spread rapidly throughout Europe, and is assumed to have crossed over to the Asian continent in the 1980s. The coronavirus-analog initially designated as CV777 was identified as the causative agent in Belgium in 1978.

In order to prevent such PED, the need to develop a subunit vaccine as a safer, more economical, and more quickly acting strategy in the onset of a disease is emerging. The subunit vaccine is used as an antigen protein of a vaccine by mass production of a structural or non-structural protein with known antigenicity, which constitutes a pathogenic microorganism, in recombinant microorganisms (*E. coli* or a different expression system).

In Korea, live attenuated PED vaccines are generally used, but the biggest problem of such vaccines is that, although attenuated, viruses are alive, so they recover their toxicity and become pathogenic, and thus may have problems in safety. In addition, in the development of a vaccine, for attenuation, it takes relatively a long time to subculture 100 times in animal cells, so it is difficult to respond quickly to viruses with a high mutation rate and the cost for vaccine development is also relatively high because of the use of animal cell culture.

Meanwhile, vaccines for preventing such disease are produced generally using animal cells, rather than bacteria due to protein folding or glycosylation. However, since the method of producing a vaccine using animal cells needs a large amount of costs for facility expansion for mass production, vaccine production is not easy, and most vaccines are expensive. In addition, inactivated virus vaccines produced using animal cells are not only difficult to store, but also have the disadvantage of being highly likely to be contaminated with viruses that can infect animals. However, unlike animal cells, since plant cells have a very low possibility of being contaminated with viruses that can infect animals, can be mass-produced at any time as long as a cultivation area is secured, and stored for a long-time in a plant body, it is expected that stable and inexpensive vaccine production is possible.

DISCLOSURE

Technical Problem

The present invention is deduced to solve the above-described problems according to the conventional art, and directed to providing a recombinant PED virus protein that not only enables efficient production using a plant body, but also exhibits high immunogenicity and virus neutralization ability, a vaccine composition including the same, and a method of preparing the protein.

However, technical problems to be solved in the present invention are not limited to the above-described problems, and other problems which are not described herein will be fully understood by those of ordinary skill in the art from the following descriptions.

Technical Solution

The present invention provides a PED virus vaccine composition, which includes a PED virus protein having an amino acid sequence represented by SEQ ID NO: 5 as an active ingredient. The PED virus protein may also include a functional equivalent of the amino acid sequence represented by SEQ ID NO: 5 in the scope of the present invention, and the functional equivalent refers to a polypeptide which has at least 60% or more, preferably 70% or more, more preferably 80% or more, and most preferably 90% or more sequence homology with the amino acid sequence as a result of the addition, substitution or deletion of an amino acid, and exhibits a substantially the same activity as the amino acid sequence represented by SEQ ID NO: 5, and as long as it is an amino acid sequence of a PED virus protein that can be stably produced using a plant body, the present invention is not limited thereto.

In addition, the present invention provides a feed composition for preventing or treating PED, which includes the PED virus protein as an active ingredient.

In addition, the present invention provides a method of preventing or treating PED by administering the PED virus protein into an individual.

In addition, the present invention provides a use of the PED virus protein for preventing or treating PED.

In addition, the present invention provides a use of the PED virus protein for preparing a PED vaccine or drug.

In addition, the present invention provides a vector for expressing a PED virus protein, which includes a polynucleotide encoding an amino acid sequence represented by SEQ ID NO: 5. The polynucleotide is preferably a polynucleotide sequence represented by SEQ ID NO: 1.

In one embodiment of the present invention, in the vector, a promoter gene and a polynucleotide encoding the amino acid sequence represented by SEQ ID NO: 5 may be operably linked sequentially.

Figure 1:
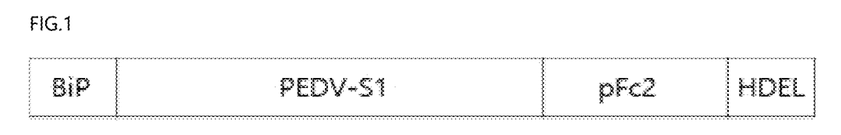
FIG. 1 shows the arrangement of genes for expressing a PED virus S1 (PEDV-S1) protein in a plant body according to one embodiment of the present invention.

In another embodiment of the present invention, the vector may have a structure shown in FIG. 1, but the present invention is not limited thereto.

In still another embodiment of the present invention, the vector may further include a gene encoding one or more selected from the group consisting of an endoplasmic reticulum (ER) signal peptide, an Fc fragment and a chaperone binding protein (BiP), but the present invention is not limited thereto.

In yet another embodiment of the present invention, the ER signal peptide may be one selected from the group consisting of peptide sequences represented by KDEL, HDEL, SEKDEL, KHEDL, KEEL, and SEHEDL, but the present invention is not limited thereto.

In yet another embodiment of the present invention, the promoter may be a cauliflower mosaic virus-derived 35S promoter, a cauliflower mosaic virus-derived 19S RNA promoter, a plant actin protein promoter, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, a pEMU promoter, a MAS promoter, a histone promoter, or a Clp promoter, but the present invention is not limited thereto.

In yet another embodiment of the present invention, a recombinant expression vector may further include a polynucleotide encoding a chaperone binding protein (BiP), a gene encoding a His-Asp-Glu-Leu (HDEL) peptide, and a gene encoding a porcine immunoglobulin Fc fragment.

In addition, the present invention provides a transformant which is transformed with the vector.

In one embodiment of the present invention, the transformant is preferably a microorganism such as E. coli, Bacillus, Salmonella or a yeast, insect cells, animal cells including human cells, an animal such as a mouse, a rat, a dog, a monkey, a pig, a horse or a cow, Agrobacterium tumefaciens, or a plant, and more preferably, a food crop such as rice, wheat, barley, corn, bean, potato, red bean, oat or sorghum; a vegetable crop such as Arabidopsis, Chinese cabbage, radish, red pepper, strawberry, tomato, watermelon, cucumber, cabbage, oriental melon, pumpkin, green onion, onion, or carrot; a specialty crop such as ginseng, tobacco, cotton, sesame, sugar cane, sugar beet, perilla, peanut or rapeseed; a fruit tree such as an apple tree, a pear tree, a date tree, peach, grape, tangerine, persimmon, plum, apricot or banana; and a flower such as a rose, a carnation, a chrysanthemum, lily, or tulip, but as long as the transformant is an organism that can be transformed with the vector of the present invention, the present invention is not limited thereto.

In addition, the present invention provides a method of producing a PED virus protein, which includes: (a) culturing the transformant; and (b) isolating and purifying a PED virus protein from the transformant or culture solution. The transformant is preferably a cell itself, a plant body or a cultured product including cells, and the culture solution is preferably a culture solution from which cells are removed after cell culture. As long as the culture solution includes a recombinant antigen of the present invention, the present invention is not limited thereto.

In one embodiment of the present invention, the purification of step (b) may be purification using an aqueous fraction, but the present invention is not limited thereto.

Advantageous Effects

A recombinant PED virus S1 protein of the present invention is not only effectively expressed in a plant body, but also has high water solubility, is easily isolated and purified, and acts as an antigen in the body, thereby exhibiting high immunogenicity and virus neutralization ability. Therefore, the recombinant PED virus S1 protein is expected to be widely used in various fields. In addition, due to the significant immunogenicity and virus neutralization ability in the body, the recombinant PED virus S1 protein can be used as a novel PED vaccine composition.

MODES OF THE INVENTION

In the present invention, using a gene of a PED virus protein represented by SEQ ID NO: 1, it was confirmed that a PED virus protein having high immunogenicity in a plant body can be effectively produced and isolated. Accordingly, since the PED virus protein of the present invention can be stably and effectively mass-produced, it is expected to provide inexpensive and stable PED vaccines.

The "antigen" used herein is the generic term for all materials causing an immune response in the body, and preferably a virus, a chemical, a bacterium, a pollen, a cancer cell, shrimp, or a partial peptide or protein thereof, and as long as the material is any material that can cause an immune response in the body, the present invention is not limited thereto.

The "porcine epidemic diarrhea (PED) virus" used herein belongs to the family of Coronaviridae, and has single-stranded RNA as a genome, a length of approximately 28 Kb, and encodes three main constituent proteins, such as a spike protein, a membrane or envelope protein, and a nucleocapsid protein. The term "spike protein" used herein is a main constituent protein of the PED virus, and has biologically important functions of recognizing target cells and fusing a cellular membrane with the virus. A partial gene of the spike protein may be used as an attenuated antigenic determinant (neutralization epitope), and in the maturation process, the spike protein is frequently cleaved into a receptor-binding subunit S1 and a membrane-binding subunit S2. Particularly, the S1 domain of the S protein may include a receptor-binding domain (RBD) mediating specific binding for a cell receptor.

The term "vaccine" used herein is a biological agent containing an antigen causing an immune response to a living body, and refers to an immunogen which generates immunity in the living body by injection or oral administration into a human or animal to prevent an infectious disease. The animal is a human or a non-human animal, and the non-human animal refers to a pig, a cow, a horse, a dog, a goat or sheep, but the present invention is not limited thereto.

The term "expression vector" used herein refers to a vector that can express a peptide or protein encoded by a heterologous nucleic acid inserted into the vector, and preferably, a vector manufactured to express a porcine Fc fragment-fused target antigen (in the present invention, a PED virus protein). The "vector" refers to any medium for introducing and/or transferring a base into a host cell in vitro, ex vivo or in vivo, and may be a replicon to which a different DNA fragment is bound to induce the replication of the bound fragment, and the "replicon" is a genetic unit (e.g., a plasmid, a phage, a cosmid, a chromosome, or a virus) which serves as a self-unit of DNA replication in vivo, that is, is replicable by being self-controlled. The recombinant expression vector of the present invention preferably includes a promoter, which is a transcription initiating factor to which an RNA polymerase binds, an optional operator sequence for regulating transcription, a sequence encoding a suitable mRNA ribosome-binding site and a sequence that regulates the termination of transcription and translation, and a terminator, more preferably, further includes a M17 5' UTR site gene for increasing a protein synthesis level, a BiP gene for transferring a target protein to the ER, an Fc fragment that increases an expression level and solubility of a target protein, an ER signal peptide (the same meaning as ER targeting sequence) gene that minimize degradation of a protein for the protein to be stably maintained in the ER, and a cloning site, and still more preferably, further includes a tag gene for easily isolating a recombinant protein, and a marker gene for selecting an antibiotic-resistant gene to select a transformant.

The "PED virus protein" used herein may include an amino acid sequence of SEQ ID NO: 5, and preferably, is represented by the amino acid sequence of SEQ ID NO: 5. According to one embodiment of the present invention, due to having high solubility, the PED virus protein is easily isolated and purified, inhibits the aggregation of a recombinant protein, and thus is effective for maintaining the physiological or pharmacological activity of a recombinant protein.

In addition, the protein of the present invention may be encoded by a gene base sequence represented by SEQ ID NO: 1. In addition, the gene variant is included in the scope of the present invention. Specifically, the gene may include a base sequence having 70% or more, more preferably, 80% or more, and most preferably, 90% or more sequence homology with the base sequence of SEQ ID NO: 1. For example, the protein of the present invention includes a polynucleotide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence homology.

The "BiP gene" is a part of a BiP sequence used to move the expressed recombinant protein to the ER, and is preferably a gene including a base sequence of SEQ ID NO: 2, and most preferably a gene represented by SEQ ID NO: 2, and consists of a base sequence having 80% or more, more preferably, 90% or more, and still more preferably 95% or more sequence homology with the base sequence of SEQ ID NO: 2. The "% in sequence homology" with respect to a polynucleotide is identified by comparing a comparative region with the optimally aligned sequence, and in the comparative region, a part of the polynucleotide sequence may include an addition or deletion (that is, a gap) compared with the reference sequence (without an addition or deletion) for the optimal alignment of the sequence. The "BIP gene" is used to move the expressed recombinant protein to the ER, and may only have some amino acids remaining after a part of the sequence is deleted when expressed.

The "ER signal peptide" refers to an amino acid sequence which allows a protein to be recognized by signal recognition particles on the ER to translocate into the ER lumen. In the present invention, there is no limitation to the type and amino acid sequence of the ER signal peptide, as long as it is a plant ER signal peptide known to those of ordinary skill in the art, and examples of the ER signal peptide in the documents disclosed in US 20130295065 and WO2009158716 may be referenced. In the present invention, the "ER signal peptide" is preferably any one polypeptide selected from the group consisting of KDEL (SEQ ID NO: 6), HDEL (SEQ ID NO: 7), SEKDEL (SEQ ID NO: 8), KHEDL (SEQ ID NO: 9), KEEL (SEQ ID NO: 10), and SEHEDL (SEQ ID NO: 11), and most preferably, a polypeptide represented by HDEL (His-Asp-Glu-Leu, SEQ ID NO: 7), and encoded by SEQ ID NO: 4. In addition, as the ER signal peptide of the present invention, a variant of SEQ ID NO: 4 is included in the scope of the present invention. Specifically, the gene consists of a base sequence having preferably 90% or more, more preferably, 95% or more, and most preferably 98% or more sequence homology with the base sequence of SEQ ID NO: 4. The "% in sequence homology" with respect to a polynucleotide is identified by comparing a comparative region with the optimally aligned sequence, and in the comparative region, a part of the polynucleotide sequence may include an addition or deletion (that is, a gap) compared with the reference sequence (without an addition or deletion) for the optimal alignment of the sequence. A binding site of the ER signal peptide is characterized by being added (or linked) to the C-terminus of a protein to be expressed or synthesized in plant cells.

The "Fc fragment" refers to a part of an immunoglobulin without an antigen-binding site, which remains after only heavy chains (H chains) are linked by S—S bonds when the immunoglobulin is digested by papain, and the Fc fragment of the present invention is preferably a porcine Fc fragment, and more preferably, a porcine Fc fragment represented by SEQ ID NO: 3. However, there is no limitation as long as it is an Fc fragment which increase an expression level and solubility of a target protein when fused with the target protein. In addition, as the Fc fragment of the present invention, a variant of SEQ ID NO: 3 is included in the scope of the present invention. Specifically, the gene consists of a base sequence having preferably 90% or more, more preferably 95% or more, and most preferably 98% or more sequence homology with the base sequence of SEQ ID NO: 3. The "% in sequence homology" with respect to a polynucleotide is identified by comparing a comparative region with the optimally aligned sequence, and in the comparative region, a part of the polynucleotide sequence may include an addition or deletion (that is, a gap) compared with the reference sequence (without an addition or deletion) for the optimal alignment of the sequence.

The "cloning site" encompasses inserts for linking/distinguishing genes in a vector, and is preferably a region represented by "ggatcctg" or "ccccgggca" in SEQ ID NO: 12, "RIL, Arg Ile Leu" located at the $8^{th}$ to $10^{th}$ positions of SEQ ID NO: 13, or "PRA, Pro Arg Ala" located at $727^{th}$ to $729^{th}$ positions of SEQ ID NO: 13, but the present invention is not limited thereto.

In the present invention, the viral protein is preferably provided in a fused form with an Fc fragment. The term "fusion" means both chemical and genetic fusion, and in the present invention, preferably, refers to genetic fusion. The "genetic fusion" refers to a link that is formed by a linear covalent bond formed through the genetic expression of a DNA sequence encoding a protein.

The gene for tagging may include, for example, an Avi tag, a calmodulin tag, a polyglutamate tag, an E tag, a FLAG tag, a HA tag, a His tag, a Myc tag, a S tag, a SBP tag, an IgG-Fc tag, a CTB tag, a Softag 1 tag, a Softag 3 tag, a Strep tag, a TC tag, a V5 tag, a VSV tag, and an Xpress tag, and the IgG-Fc tag may be derived from a human, a mouse, a rabbit or a pig.

A marker gene for selection may be, for example, a herbicide-resistant gene such as glyphosate or phosphinothricin, an antibiotic-resistant gene such as kanamycin, G418, bleomycin, hygromycin or chloramphenicol, or an aadA gene, and the promoter may be, for example, a pEMU promoter, a MAS promoter, a histone promoter, a Clp promoter, a cauliflower mosaic virus-derived 35S promoter, a cauliflower mosaic virus-derived 19S RNA promoter, a plant actin protein promoter, a ubiqitin protein promoter, a cytomegalovirus (CMV) promoter, a simian virus 40 (SV40) promoter, a respiratory syncytial virus (RSV) promoter, or an elongation factor-1 alpha (EF-1α) promoter, and the terminator may be, for example, a nopaline synthase (NOS) terminator, a rice amylase RAmy1 A terminator, a faceolin terminator, a terminator of an octopine gene of *Agrobacterium tumafaciens*, or an rmB1/B2 terminator of *E. coli*, but the present invention is not limited thereto.

The "vector" used herein may have a structure shown in FIG. 1, but the present invention is not limited thereto.

The "vector" used herein is preferably a gene having an amino acid sequence SEQ ID NO: 13, and most preferably an amino acid sequence represented by SEQ ID NO: 13, and consists of an amino acid sequence having 80% or more, more preferably 90% or more, and still more preferably 95% or more sequence homology with the sequence of SEQ ID NO: 13.

In addition, the amino acid sequence may be encoded by a gene sequence represented by SEQ ID NO: 12, but the present invention is not limited thereto. Specifically, the gene may consist of a base sequence having 90% or more, more preferably 95% or more, and most preferably 98% or more sequence homology with the base sequence of SEQ ID NO: 12. The "% in sequence homology" with respect to a polynucleotide is identified by comparing a comparative region with the optimally aligned sequence, and in the comparative region, a part of the polynucleotide sequence may include an addition or deletion (that is, a gap) compared with the reference sequence (without an addition or deletion) for the optimal alignment of the sequence.

The "transformation" used herein encompasses a change in genetic properties of a living organism by injected DNA, the "transgenic organism" is a living organism produced by injecting an external gene through a molecular genetic method, and preferably, a living organism transformed by a recombinant expression vector of the present invention. The living organism is a living thing such as a microorganism, a eukaryotic cell, an insect, an animal or a plant without limitation, and preferably, *E. coli, Salmonella, Bacillus*, yeast, an animal cell, a mouse, a rat, a dog, a monkey, a pig, a horse, a cow, *Agrobacterium tumefaciens* or a plant, but the present invention is not limited thereto.

The "plant" used herein is a plant that can produce a protein in a large amount, and more specifically, may be selected from the group consisting of tobacco, *Arabidopsis thaliana*, corn, rice, soybean, canola, alfalfa, sunflower, sorghum, wheat, cotton, peanut, tomato, potato, lettuce and pepper, and preferably tobacco. The tobacco in the present invention is a *Nicotiana* genus plant, which can overexpress a protein, but there is no particular limitation on the type of tobacco, and the present invention may be implemented by selecting a suitable species for a transforming method and the purpose of mass-production of a protein. For example, a species such as *Nicotiana benthamiana* L. or *Nicotiana tabacum* cv. Xanthi may be used.

The transformant may be prepared by transformation, transfection, *Agrobacterium*-mediated transformation, particle gun bombardment, sonication, electroporation and polyethylene glycol (PEG)-mediated transformation, but there is no limitation as long as the transformant is prepared by any method of injecting the vector of the present invention.

The "solubility" used herein refers to a degree of solubilizing a target protein or peptide in a solvent suitable for being administered to the human body. Specifically, the solubility indicates a degree of saturation of a solute in a given solvent at a specific temperature. The solubility may be measured by determining a saturation concentration of a solvent, and for example, the solubility may be determined by adding an excessive amount of solute in a solvent, stirring and filtering the solution, and measuring a concentration using an UV spectrophotometer or HPLC, but the present invention is not limited thereto. High solubility is preferable for isolation and purification of a recombinant protein, and has advantages of inhibition of the aggregation of the recombinant protein and maintenance of physiological or pharmacological activity of the recombinant protein.

The "prevention" used herein refers to all actions of inhibiting or delaying the occurrence of PED by administration of a recombinant PED virus protein according to the present invention.

The "treatment" used herein refers to all actions involved in improving or beneficially changing symptoms of PED by administration of a protein according to the present invention.

The "individual" used herein refers to a subject to which a recombinant PED virus protein of the present invention can be administered, but the individual is not limited.

The "vaccine composition" used herein may be formulated in an oral preparation such as such as a powder, granules, a tablet, a capsule, a suspension, an emulsion, a syrup, or an aerosol, or a sterile injectable solution according to a conventional method. The vaccine composition may be formulated with a diluent or an excipient such as a filler, a thickening agent, a binder, a wetting agent, a disintegrant, a surfactant, which are conventionally used. A solid preparation for oral administration may be a tablet, pill, powder, granule or capsule, and such a solid formulation may be obtained by mixing at least one of excipients such as starch, calcium carbonate, sucrose, lactose and gelatin with a lecithin-like emulsifier. In addition, in addition to the simple excipient, lubricants such as magnesium stearate and talc may also be used. As a liquid preparation for oral administration, a suspending agent, a liquid for internal use, an emulsion or a syrup is used, and other than a commonly used simple diluent such as water or a liquid paraffin, various excipients, for example, a wetting agent, a sweetening agent, a fragrance and a preservative may be included. As a preparation for parenteral administration, a sterile aqueous solution, a non-aqueous agent, a suspending agent, an emulsifier, or a freeze-drying agent is included. As a non-aqueous agent or suspending agent, propylene glycol, polyethylene glycol, a vegetable oil such as olive oil, or an injectable ester such as ethyl oleate may be used.

In addition, the "adjuvant" used herein generally refers to any material increasing a humoral and/or cellular immune response to an antigen. Here, the vaccine composition of the present invention may further include an "adjuvant." The adjuvant may be, for example, a complete Freund's adjuvant (CFA), an incomplete Freund's adjuvant (IFA), alum, oil, Lipid A, monophosphoryl lipid A, a bacterial agent such as *Bacillus*-Calmette-Guerrin (BCG), a nucleic acid such as CpG-DNA, dsRNA, a bacterial component agent such as tuberculin, a natural high molecular material such as keyhole limpet hemocyanin or yeast mannan, a muramyl tripeptide or a muramyl dipeptide or a derivative thereof, alum, a nonionic block copolymer, or a cytokine such as interleukin 2 (IL-2), granulocyte macrophage colony stimulating factor (GM-CSF), interferon-α (IFN-α), or interferon-0 (IFN-0), and a combination of at least one or two thereof, and in one embodiment of the present invention, an IMS1313 oil adjuvant was used.

The vaccine composition or pharmaceutical composition of the present invention may be formulated in an oral preparation such as a powder, granules, a tablet, a capsule, a suspension, an emulsion, a syrup or an aerosol, a preparation for external use, a suppository or a sterile injectable solution.

Administration routes for the vaccine composition according to the present invention may include, but are not limited to, oral, intravenous, intramuscular, intraarterial, intramedullary, intradural, intracardiac, transdermal, subcutaneous, intraperitoneal, intranasal, enteral, local, sublingual or rectal administration. Oral or parenteral administration is preferable. The term "parenteral" used herein means subcutaneous, intradermal, intravenous, intramuscular, intraarticular, intrabursal, intrastemal, intradural, intralesional and intracranial injection techniques. The vaccine composition of the present invention may be administered in the form of a suppository for rectal administration.

A dosage of the vaccine composition or pharmaceutical composition of the present invention is selected in consideration of an individual's age, weight, sex, or body condition. The amount required for inducing an immunoprotective response in an individual without a separate side reaction may vary according to the presence of any recombinant protein used as an immunogen and any excipient. Generally, each dose contains 0.1 to 1000 µg, and preferably, 0.1 to 100 µg of the recombinant protein of the present invention per mL of a sterile solution. In the case of the vaccine composition, if necessary, optionally repeated antigen stimulation may be performed after an initial dose.

The "feed composition" used herein is a feed including a recombinant PED virus S1 protein of the present invention, and the feed may be a byproduct of pork, beef or chicken as well as corn, rice, common rice straw, wild grass, grass, ensilage, dry grass, or native grass, but the present invention is not limited thereto, and there is no limitation as long as it is a feed used for raising livestock. Methods for adding and mixing a recombinant PED virus S1 protein of the present invention with such a feed may include mechanical mixing, adsorption and occlusion, but the present invention is not limited thereto.

Hereinafter, to help in understanding the present invention, exemplary examples will be suggested. However, the following examples are merely provided to more easily understand the present invention, and not to limit the present invention.

EXAMPLES

Example 1: Construction of Recombinant PED Virus S1 (PEDV-S1) Protein Plant Expression Vector A recombinant plant expression vector was constructed to express a PED virus S1 protein in a plant body as shown in FIG. 1. More specifically, gene information for the PED virus S1 protein was secured, and a gene of SEQ ID NO: 1 was synthesized as a sequence optimized for expression in *Nicotiana benthamiana*. A PED virus S1 protein plant expression vector was constructed by sequentially linking a polynucleotide (SEQ ID NO: 2) encoding a chaperone binding protein (BiP) signal peptide, a polynucleotide (SEQ ID NO: 1) encoding a PED virus S1 protein, a polynucleotide (SEQ ID NO: 3) encoding pFc2, which is an Fc fragment (porcine immunoglobulin Fc fragment (pFc) and a polynucleotide (SEQ ID NO: 4) encoding a His-Asp-Glu-Leu (HDEL) peptide between a CaMV 35S promoter gene and an NOS terminator of a pCAMBIA1300 vector.

Example 2: Confirmation of Expression of Recombinant PEDV S1 Protein 2.1. Transient Expression of Plant Expression Vector The plant expression vector prepared in Example 1 was transformed into the *Agrobacterium* strain LBA4404 by electroporation. The transformed *Agrobacterium* was cultured with shaking in 5 mL of a yeast extract peptone (YEP) liquid medium (10 g of yeast extract, 10 g of peptone, 5 g of NaCl, 50 mg/L of kanamycin, and 25 mg/L of rifampicin) at 28° C. for 16 hours, 1 mL of a primary culture solution was inoculated into 50 mL of a fresh YEP medium and cultured with shaking at 28° C. for 6 hours. The cultured *Agrobacterium* was collected through centrifugation (7,000 rpm, 4° C., 5 min), and resuspended in an infiltration buffer (10 mM MES (pH 5.7), 10 mM $MgCl_2$, 200 µM acetosyringone) to an O.D. of 1.0 at a wavelength of 600 nm. The *Agrobacterium* suspension was injected into the back side of a *Nicotiana benthamiana* leaf using a needle-free syringe to perform Agro-infiltration.

2.2. Confirmation of Expression of Recombinant PED Virus S1 Protein in Plant Body A protein was extracted from the plant leaf prepared in Example 2.1 and centrifuged, and then a protein in an aqueous fraction (S) contained in a solution and a protein in a pellet (P) fraction were identified by western blotting. More specifically, 30 µL of each fraction was mixed with an SDS sample buffer, and then heated. In addition, the fraction was loaded on a 10% SDS-PAGE gel for electrophoresis to isolate proteins by size, and the isolated protein was transferred to a PVDF membrane and blocked with 5% skim milk, an anti-pig secondary antibody recognizing pFc2 was bound to the membrane, and treated with an ECL solution according to a method provided by a manufacturer to identify the expression of the recombinant PED virus S1 protein. The result is shown in FIG. 2.

Figure 2:
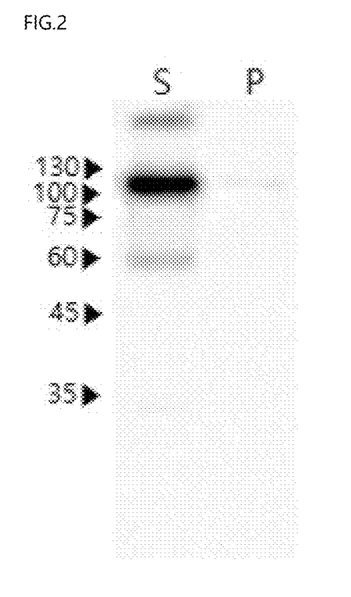
FIG. 2 shows the result of confirming the expression of a PEDV S1 protein in a plant body through western blotting according to one embodiment of the present invention.

As shown in FIG. 2, it was confirmed that most of the expressed recombinant PED virus S1 protein is present in the aqueous fraction.

From the above result, it was confirmed that the vector for expressing a recombinant PED virus S1 protein of the present invention can effectively express the recombinant PED virus S1 protein in a plant body, and since the recombinant PED virus S1 protein prepared using the vector has high solubility, it is easily isolated and purified, and the aggregation of the recombinant protein is inhibited to be effective in maintaining physiological or pharmacological activity of the recombinant protein.

Example 3: Isolation and Purification of Recombinant PEDV S1 Protein 200 mL of a protein extraction solution (50 mM Tris (pH 7.2), 150 mM NaCl, 0.1% Triton X-100, 1× protease inhibitor) was added to the 40 g of the *Nicotiana ventamia* prepared in Example 2.1, the mixture was subjected to tissue disruption using a blender, and centrifuged at 13,000 rpm for 20 minutes at 4° C. to recover a protein extract. For isolation and purification of the expressed recombinant PED virus protein, affinity chromatography was performed with a column filled with a protein A-sepharose resin. The column was filled with 5 mL of the resin, and equilibrated with 50 mL of a washing solution (50 mM Tris (pH 7.2), 150 mM NaCl). After the recovered protein extract was applied to the column, 100 mL of a washing solution was flowed to wash the resin, the recombinant protein was eluted with an elution solution (0.1 M sodium citrate (pH 3.0), 150 mM NaCl), and the protein eluate was neutralized by adding a neutralization solution (1 M Tris (pH 9.0)). The elution solution containing the recombinant protein was replaced with physiological saline (PBS) using a 30 kD-sized filter and concentrated, thereby obtaining an isolated and purified recombinant PED virus protein. The isolated and purified protein was confirmed by Coomassie staining after SDS-PAGE (FIG. 3).

Figure 3:
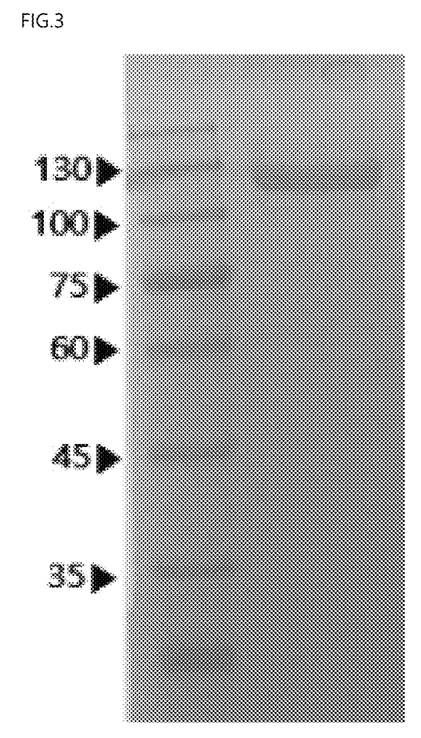
FIG. 3 shows the result of isolating and purifying a PEDV S1 protein according to one embodiment of the present invention.

As shown in FIG. 3, it was confirmed that the recombinant protein having a size of approximately 120 Kd was purified.

The recombinant protein of the present invention was well purified without a large difference from the conventional protein. Such a result shows that, when the protein was expressed in a plant, a problem of being likely to reduce production efficiency due to a modified sugar structure was not found, and the protein according to the present invention is well produced in a plant.

Example 4: Confirmation of Immunogenicity of PEDV S1 Protein Expressed in Plant

To confirm whether the recombinant PED virus S1 protein antigen induces an antibody in vivo and thus has immunogenicity, experiments were carried out with five 6-week-old female guinea pigs per group. More specifically, for a negative control, physiological saline was administered, for a positive control, a commercially available PED vaccine (Joongang Vaccine) was administered, and for an experimental group, the recombinant PED virus S1 protein was subcutaneously administered at a dose of 150 μg twice every three weeks. Upon injection of the antigen, the same amount of an IMS1313 adjuvant (SEPPIC) was mixed and injected. Blood was collected from the jugular vein or heart before antigen administration and at two weeks after the second administration, followed by isolating a serum, and storing it in a refrigerator at −20° C. The production of a specific antibody against the PEDV S1 protein in each serum was identified using an ELISA plate coated with a His tag-fused PEDV-S1 recombinant protein, and the result is shown in FIG. 4.

Figure 4:
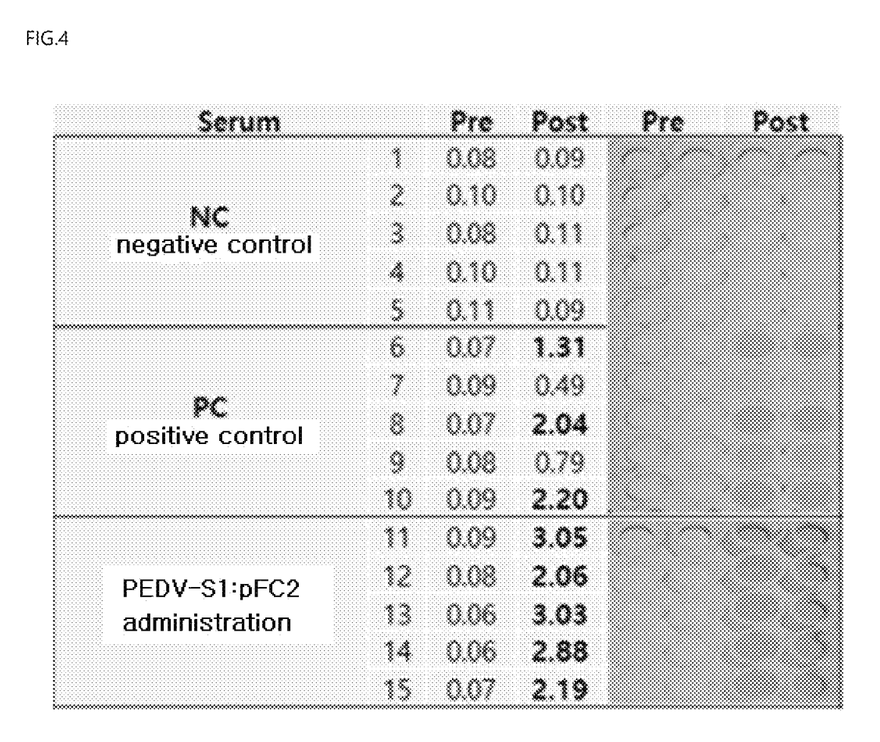
FIG. 4 shows the result of confirming immunogenicity after an antigen of a recombinant PEDV S1 protein is administered twice according to one embodiment of the present invention.

As shown in FIG. 4, it was confirmed that no reactivity to the recombinant PED virus S1 protein was observed in the serum of an untreated group, but reactivity to the PED virus S1 protein is shown in the serum of the group in which the commercially-available vaccine or the recombinant antigen protein was administered twice, and compared to the commercial vaccine-administered group, the group administered the recombinant antigen protein showed a relatively higher specific antibody production rate.

Example 5: Confirmation of Neutralizing Antibody Titer in Blood

It was confirmed whether blood antibodies induced by the administration of the recombinant antigen protein have PED virus neutralization ability using the serum prepared in Example 4. More specifically, in the neutralizing antibody test, a PEDV QIAP1401 strain virus and Vero cells as an infection host were used. Serum was isolated from the collected blood, immobilized at 57° C. for 30 minutes, and then diluted 2-fold with Minimum Essential Media (MEM) Eagle containing 10 μg/ml of trypsin. Equal amounts of 316 $TCID_{50}$/0.1 mL of the PEDV virus and the diluted serum were mixed for neutralization at 37° C. for 90 minutes. Immediately before the end of culture, the Vero cells prepared in a monolayer state in a 96-well plate were washed with PBS three times, 100 uL of the serum-virus mixture was added, and then cultured at 37° C. for 2 hours. After culture, 100 uL of a medium containing 2 μg/mL trypsin was added, and the virus was cultured at 37° C. for 3 to 5 days until a cytopathic effect (CPE) was exhibited. A neutralizing antibody titer was measured by observing the serum dilution factor of a well immediately before the CPE was exhibited under a microscope (Table 1).

As a result, a neutralizing antibody titer by the recombinant PEDV-S1 antigen protein is 16.0 (Log 2) on average, and a neutralizing antibody titer by the commercially available vaccine is 7.2 (Log 2), showing that the formation of neutralizing antibody titer by the recombinant PEDV-S1 antigen protein is higher than that by the commercially available vaccine.

TABLE 1

| Administered antigen | No. | Neutralizing antibody titer |
|---|---|---|
| Physiological saline | 1 | <4 |
| | 2 | <4 |
| | 3 | <4 |
| | 4 | <4 |
| | 5 | <4 |
| Commercial vaccine | 6 | 8 |
| | 7 | 4 |
| | 8 | 8 |
| | 9 | 8 |
| | 10 | 8 |
| PEDV-S1:pFc2 | 11 | 16 |
| | 12 | 16 |

From the above results, it was confirmed that the recombinant PED virus S1 protein of the present invention is not only effectively expressed in a plant body, but also has high water solubility, and thus the protein is easily isolated and purified, and serves as an antigen in the body, thereby exhibiting high immunogenicity and virus neutralization ability. Therefore, it was confirmed that the protein can be used as a novel PED vaccine composition.

Hereinafter, preparation examples of the pharmaceutical composition and feed composition of the present invention will be described, but the examples are merely provided to specifically described the present invention, rather than limit the invention.

Preparation Example 1. Preparation of Pharmaceutical Composition 1.1. Preparation of Powder

TABLE 2

| Recombinant PED virus S1 protein | 20 mg |
|---|---|
| Lactose | 100 mg |
| Talc | 10 mg |

A powder was prepared by mixing the above components and filling an airtight pouch with the mixture.

1.2. Preparation of Tablet

TABLE 3

| | |
|---|---|
| Recombinant PED virus S1 protein | 10 mg |
| Corn starch | 100 mg |
| Lactose | 100 mg |
| Magnesium stearate | 2 mg |

A tablet was prepared by mixing the above components and compounding the mixture according to a conventional method of preparing a tablet.

1.3. Preparation of Capsule

TABLE 4

| | |
|---|---|
| Recombinant PED virus S1 protein | 10 mg |
| Crystalline cellulose | 3 mg |
| Lactose | 14.8 mg |
| Magnesium stearate | 0.2 mg |

A capsule was prepared by mixing the above components and filling a gelatin capsule with the mixture according to a conventional method of preparing a capsule.

1.4. Preparation of Injectable Preparation

TABLE 5

| | |
|---|---|
| Recombinant PED virus S1 protein | 10 mg |
| Mannitol | 180 mg |
| Sterile distilled water for injection | 2,974 mg |
| Na$_2$HPO$_4$2H$_2$O | 26 mg |

An injectable preparation was prepared with the above contents of the components per ampoule (2 mL) according to a conventional method of preparing an injectable preparation.

1.5. Preparation of Liquid

TABLE 6

| | |
|---|---|
| Recombinant PED virus S1 protein | 20 mg |
| Isomerized sugar | 10 g |
| Mannitol | 5 g |
| Purified water | q.s. |

A liquid was prepared by adding and dissolving each component in purified water, adding an appropriate amount of a lemon flavor and mixing them together, adding purified water thereto to a total volume of 100 mL, and then pouring the resulting solution into a brown bottle and sterilizing the solution according to a conventional method of preparing a liquid.

Preparation Example 2. Preparation of Feed Composition

TABLE 7

| | |
|---|---|
| Recombinant PED virus S1 protein | 100 mg |
| Vitamin E | 0.7 mg |
| L-carnitine | 0.7 mg |

A feed was prepared by mixing the above components according to a conventional feed preparation method.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

As a recombinant PED virus S1 protein of the present invention may be effectively expressed in a plant body, and have high water solubility, it is easily isolated and purified, and also serves as an antigen in the body to exhibit high immunogenicity and virus neutralization ability, and therefore it is expected to be used in various fields. Moreover, due to significant immunogenicity and virus neutralization ability in the body, the protein is expected to be used as a novel PED vaccine composition, and thus is available in the industry.

The invention claimed is:

1. A method for preventing or treating porcine epidemic diarrhea, the method comprising administering, to an animal except a human, a composition comprising a porcine epidemic diarrhea virus protein consisting of the amino acid sequence set forth in SEQ ID NO:5.

2. A vector comprising a polynucleotide encoding a porcine epidemic diarrhea virus protein consisting of the amino acid sequence set forth in SEQ ID NO: 5.

3. The vector of claim 2, further comprising:
a gene encoding one or more selected from the group consisting of an endoplasmic reticulum signal peptide, a Fc fragment and a chaperone binding protein (BiP).

4. The vector of claim 3, wherein the endoplasmic reticulum signal peptide is one selected from the group consisting of the peptide sequences represented by KDEL (SEQ ID NO:6), HDEL (SEQ ID NO:7), SEKDEL (SEQ ID NO:8), KHEDL (SEQ ID NO:9), KEEL (SEQ ID NO:10), and SEHEDL (SEQ ID NO:11).

5. A transformant which is transformed with the vector of claim 4.

6. The transformant of claim 5, which is a plant.

7. A method of producing a porcine epidemic diarrhea virus protein, comprising:
(a) culturing the transformant of claim 5; and
(b) isolating and purifying a porcine epidemic diarrhea virus protein from the transformant or culture solution.

8. The method of claim 7, wherein the purification in Step (b) is purification using an aqueous fraction.

* * * * *